United States Patent [19]

Shifriss

[11] Patent Number: 4,686,319
[45] Date of Patent: Aug. 11, 1987

[54] SYNTHESIS OF GENETIC FEMALES AND THEIR USE IN HYBRID SEED PRODUCTION

[75] Inventor: Oved Shifriss, Highland Park, N.J.
[73] Assignee: Rutgers, The State University of New Jersey, New Brunswick, N.J.
[21] Appl. No.: 779,836
[22] Filed: Sep. 25, 1985
[51] Int. Cl.$^4$ .............................................. A01H 1/02
[52] U.S. Cl. ......................................... 800/1; 47/58; 47/DIG. 1
[58] Field of Search .................. 47/58, DIG. 1; 800/1
[56] References Cited

U.S. PATENT DOCUMENTS

| | | |
|---|---|---|
| 3,570,181 | 3/1971 | Davis ..................................... 47/58 |
| 3,710,511 | 1/1973 | Patterson ............................... 47/58 |
| 3,861,097 | 1/1975 | Patterson ............................... 47/58 |
| 3,971,161 | 7/1976 | Bonucci ................................. 47/58 |
| 4,254,580 | 3/1981 | Ferguson ............................... 47/58 |
| 4,326,358 | 4/1982 | Lawrence, Jr. ......................... 47/58 |
| 4,351,130 | 9/1983 | Rutger et al. .......................... 47/58 |
| 4,368,592 | 1/1983 | Welch ................................... 47/58 |
| 4,378,655 | 4/1983 | Johnson ................................. 47/58 |
| 4,406,086 | 9/1983 | Hayward ............................... 47/58 |
| 4,499,687 | 2/1985 | Lawrence et al. ....................... 47/58 |
| 4,513,532 | 4/1985 | Muirhead et al. ...................... 47/58 |
| 4,517,763 | 5/1985 | Beversdorf et al. .................... 47/58 |

OTHER PUBLICATIONS

Robinson, R. W., et al., "Genes of the Cucurbitaceae," HORT Science, vol. 11(6), Dec. 1976.
Robinson, R. W., et al., "Promotion of Pistillate Flowering in Cucurbita by 2-Chlorethylphosphonic Acid," Euphytica, 19 (1970), 180–183.
"Regulation of Sex Expression in the Cucumber," Research Reports, Feb. 1969.
Vegetable Improvement Newsletter, No. 12, Jan. 15, 1970.
Shifriss, Oved; "Origin, Expression and Significance of Gene B in Cucurbita pepo L.," J. Amer. Soc. Hort. Sci., 106(2): 220-232, 1981.
Shifriss, Oved, et al., "Sex Expression in the Cucumber," Proceedings of the American Society for Horticultural Science, vol. 67, 479-486 (1956).
Shifriss, Oved; "Sex Control in Cucumbers," The Journal of Heredity, vol. 52, No. 1, Jan.-Feb. 1961.
Shifriss, Oved, et al.; "Sensitivity of Female Inbreds of Cucumis Sativus to Sex Reversion by Gibberellin," Science, Mar. 27, 1964, vol. 143, No. 3101, 1452-1453.
Shifriss, Oved; "Do Cucurbita Plants with Silvery Leaves Escape Virus Infection? Origin and Characteristics of NJ260," Cucurbit. Genetic Coop. Rpt. 4:42-43 (1981).
Breeding Field Crops, by J. M. Poehlman, Avis Publishing Co., Inc., Westport, Conn. (1977).
Shifriss, Oved; "Conventional and Unconventional Systems Controlling Sex Variations in Ricinus, J. Genet. 57:361-388, 1960.
Pollination Mechanisms, Reproduction and Plant Breeding, by R. Frankel and E. Galun, Springer-Verlag, Berlin Heidelberg, New York (1977).
Nitsch, J. P., et al., "The Development of the Sex Expression in Cucurbit Flowers," Amer. J. Bot., 39:32-43 (1952).
Glossary of Genetics and Cytogenetics, Classical and Molecular, 4th rev. ed., by R. Rieger, M. Michaelis, and M. M. Green, Springer-Verlag, Berlin Heidelberg, New York, 1976.
Rearson, O. H., et al., 1951, Notes on Species Crosses in Curcurbita, Proc. Amer. Soc. Hort. Sci. 57:310-322.
Cucurbita, by T. W. Whitaker et al., Interscience Publications, Inc., New York, 1962.
Rhodes, A. M., 1959, Species Hybridization and Interspecific Gene Transfer in the Genus Cucurbita, Proc. Amer. Soc. Hort. Sci., 74:546-551.
Whitaker, I. N., 1956, The Origin of the Cultivated Cucurbita, American Naturalist, 90:171-176.

Primary Examiner—Robert E. Bagwill
Attorney, Agent, or Firm—Leroy G. Sinn

[57] ABSTRACT

A synthetic method is described for the development of genetic females in squash (Cucurbita pepo L.) through crosses of monoecious varieties or inbreds followed by selection. The genetic females and true-breeding female lines can be propagated sexually following chemical induction of male flowers. Such female lines can be used as seed parents in production of hybrids as well as germplasm for future breeding programs. The new synthetic method is applicable to other monoecious species of plants.

59 Claims, 7 Drawing Figures

SYNTHESIS OF GENETIC FEMALES AND THEIR USE IN HYBRID SEED PRODUCTION

Field of the Invention

This invention relates to breeding crop plants. In particular, it relates to a novel synthesis of genetic females through crosses of monoecious varieties or inbreds followed by selection. It also relates to the use of these females in hybrid seed production, and as germplasm for future breeding programs.

BACKGROUND OF THE INVENTION

Hybrid plants result from crosses between two different varieties or inbreds. Hybrids are often superior over non-hybrid varieties in vigor, yield, uniformity, as well as in other characters. And this is the main reason for their agricultural value. In producing hybrid seed, the two varieties are grown in proximity for effective pollination; one variety serves as seed parent and the other as pollen parent. Natural pollination is brought about by either wind, insects, or other animals. In the past, crossing two varieties on a large scale was a very difficult task because the plants of many crop species bear both male and female reproductive structures, i.e., they are capable of self-pollination as well as cross-pollination. Therefore, in order to prevent self-pollination and obtain pure hybrid seed, it was necessary to emasculate the seed parent by hand, a costly operation which usually requires a large number of workers. Emasculation in this case refers to a physical removal of functional male reproductive structures from the seed parent.

Different systems were devised which do away with the problem of emasculation and thus facilitate the commercial production of hybrid seed. Some effective systems are based on the use of male-sterile plants, or self-incompatible plants, or female plants as seed parents. An important feature of these systems is that they enable their male-sterile, self-incompatible, and female plants to reproduce their kind in practical ways.

These systems are as follows:

1. A group of genetic elements which controls cytoplasmic male-sterility in the seed parent, the reproduction of this seed parent by a "maintainer" line, and the restoration of male fertility in the hybrid plants. This system proved to be very successful in hybrid seed production in a number of economically important crops such as maize (corn), sorghum, and sunflower. It is described in *Breeding Field Crops* by J. M. Poehlman, Avis Publishing Company, Inc., Westport, Conn. (1977), and in other plant breeding texts.

2. Combinations of system #1 and genetic elements which either improve cross-pollination or increase the usefulness of the hybrids. Such combinations are described in U.S. Pat. Nos. 4,351,130 (1982), 4,378,655 (1983), and 4,517,763 (1985) for wheat, sunflower, and rape, respectively.

3. Clonal propagation of genetic self-incompatible plants. This is described in U.S. Pat. No. 4,499,687 (1985) for use in hybrid Brassica seed production.

4. Mutants which appear as female plants in one environment and as monoecious plants—each bearing both female and male flowers—in another environment. See Shifriss, O. (1960). "Conventional and Unconventional Systems Controlling Sex Variations in *Ricinus*". *J. Genet.* 57: 361–388.

5. Chemical agents which convert monoecious (or hermaphroditic) plants into female (or male-sterile) plants. Example: potentially monoecious plants of squash (*Cucurbita pepo* L.) can be converted into female plants by a treatment with 2-chloroethylphosphonic acid (sold under several designations including Ethephon).

6. A combination of genetic elements and chemical agents which control sex expression in plants. Example: in cucumbers (*Cucumis sativus* L.), genetic female plants can be converted into monoecious plants by treatment with either gibberellic acid ($GA_3$ or other gibberellins) or silver nitrate.

The literature on systems #5 and #6 is reviewed in *Pollination Mechanisms, Reproduction and Plant Breeding* by R. Frankel and E. Galun, Springer—Verlag, Berlin Heidelberg New York (1977). These systems are being used in commercial hybrid seed production of several members of the Cucurbitaceae family.

The present invention relates to a synthesis of genetic females as well as to the utilization of these females in squash. The name "squash" refers here to any variety of the 5 cultivated species of the botanical genus Cucurbita: *C. ficifolia* Bouché, *C. maxima* Duch., *C. mixta* Pang., *C. moschata* Poir., and *C. pepo* L. The illustrative species in which the new genetic females were synthesized is *C. pepo*.

The 5 cultivated squash species are monoecious (FIG. 1; see also Nitsch, J. P., E. B. Kurtz, Jr., J. L. Liverman, and F. W. Went. 1952. "The Development of Sex Expression in Cucurbit Flowers". *Amer. J. Bot.* 39:32–43). Although some of these species are restricted to certain ecological regions, squash has become a cosmopolitan crop. It is now grown extensively in many parts of the world, particularly by small gardeners, and its popularity as food crop is increasing.

No useful cytoplasmic male-sterile plants, or self-incompatible plants, or genetic female plants were reported in any variety of the cultivated cucurbita species. Whereas the genetic females of monoecious species of other plant genera were found to occur naturally, the new genetic females of squash were synthesized through crosses of monoecious inbreds followed by selection. But like some of the naturally occurring genetic females, the newly synthesized females can be converted into monoecious plants by chemical agents. Therefore, the new genetic females of squash can be classified under system #6.

The current commercial production of hybrid squash seed is based largely on system #5. This involves the use of Ethephon treatment for conversion of a potentially monoecious variety into a female population. And this chemically induced female population is used as seed parent in hybrid production. Bees are the main agent for cross-pollination. But the Ethephon treatment has the following shortcomings:

(1) Cost of Ethephon treatment. Two to six sprayings are often required for effective sex conversion. The number of sprayings depends on concentration, variety, and environmental conditions.

(2) Field inspections are necessary in order to determine the efficacy of the sprayings.

(3) Partial pruning of vines may be needed in order to eliminate the formation of male flowers some time after the last spraying.

(4) Ethephon treatment may slow down growth or stunt plants.

The use of the newly synthesized genetic females can obviate most of the above shortcomings.

The present invention is unique, economically valuable, and applicable to other monoecious species of plants. It is unique because it represents the first case in higher plants in which genetic females were synthesized through crosses of monoecious inbreds; it is economically valuable because it offers a more efficient method of hybrid seed production in squash than the one currently in use; and it is applicable to other monoecious species of plants because the genetic control of sex in some of these species is similar.

SUMMARY OF INVENTION

This invention relates to a novel synthesis of true-breeding female lines through crosses of monoecious inbreds followed by selection. The preferred embodiment of this invention is a single species of squash, Cucurbita pepo L.

Information gathered during the synthesis of true-breeding female lines in the preferred species of squash, and data obtained from inheritance studies of femaleness, led to a formulation of two guiding principles for synthesis of true-breeding female lines in monoecious species of crop plants.

The first principle concerns the choice of monoecious inbreds as parents for crosses. The parents should be distantly-related in breeding history and genetic make-up. And some of them should be strongly female.

The second principle concerns the requirements for selection of individual plants. Selection for female plants, or for monoecious plants of intense female expression, should preferably be done in large $F_2$ populations and/or in a large number of segregating progenies. Selection for increasing number of female flowers in plants of filial generations can lead to the discovery of genetic females. Furthermore, the $F_2$ and other segregating generations, which are subject to selection, should be grown under environmental conditions favoring strong male expression.

The discovery of genetic females may require selection in segregating generations of one or more crosses. Once a genetic female is found, it can be self-pollinated and reproduced by seed following chemical induction of male flowers. True-breeding female lines are then developed through selection and inbreeding of genetic females in subsequent generations. In this operation, selection is confined to progenies of increasingly higher frequencies of genetic females The process used for synthesis of true-breeding female lines in C. pepo is applicable to each of the 4 other squash species of Cucurbita (C. ficifolia. C. maxima, C. mixta, and C. moschata). Additionally, this process is broadly applicable to members of Cucurbitaceae family as well as to monoecious species of other crop plants which are susceptible to such synthesis.

This invention relates also to the utilization of synthesized true-breeding female lines (1) in hybrid seed production, (2) in development of new true-breeding female lines of diverse horticultural characteristics and high combining ability, and (3) in development of new monoecious varieties and hybrids such as those adapted to mechanized harvesting.

This invention should be particularly useful in squash breeding and in breeding other monoecious crops in which no reports are known of natural occurrence of genetic females or cytoplasmic male-sterile plants.

The first reproductive leaf axil is designated 1, male flower is shown as 2 and female flower having a green fruit at early bud stages is designated 3. The transitional phase is delineated by the leaf positions of $T_1$ and $T_2$, $T_1=14$ and $T_2=23$, in this illustration. In a given environment, varieties differ quantitatively in sex expression—some are strongly male and others are strongly female or intermediate, depending on the relative length of their male and transitional phases. In a given environment, varieties also differ quantitatively in onset of flowering—some are early and others are late or intermediate depending, among other things, on the sequential position of the first reproductive leaf axil.

Figure 2:
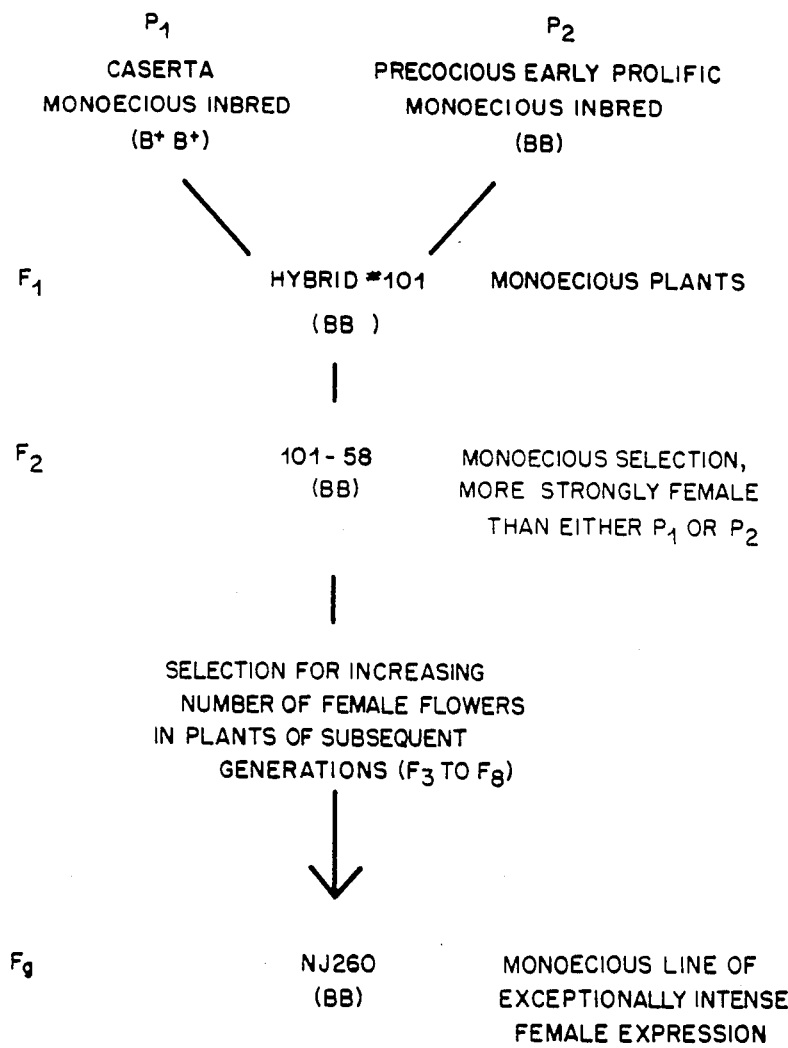

FIG. 2 illustrates the origin of NJ260 through crossing, self-pollination, and selection. NJ260 is a true-breeding monoecious line of intense female expression. Its fruits are precociously yellow (BB), like those of parent $P_2$, i.e., the fruits are yellow already at early bud stages.

Figure 3:
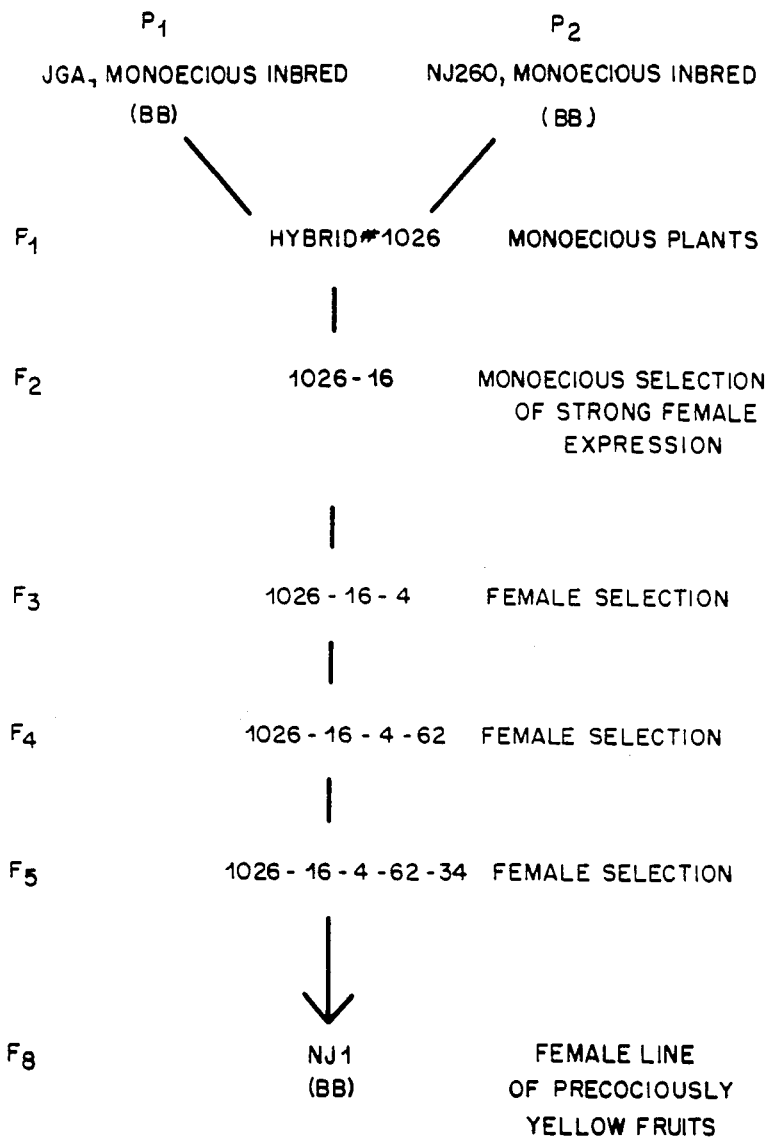

FIG. 3 illustrates the origin of NJ1 through crossing, self-pollination, and selection. NJ1 is a true-breeding genetic female line whose fruits are precociously yellow (BB), as those of its parents, i.e., the fruits are yellow already at early bud stages. The pedigree shows the relationship of individual plant selections from one generation to the next. Female plants were self-pollinated and reproduced by seed following chemical induction of male flowers. The female plants were selected for several generations until a true-breeding female line was established. For illustration of a female plant of NJ1 see FIG. 5.

Figure 4:
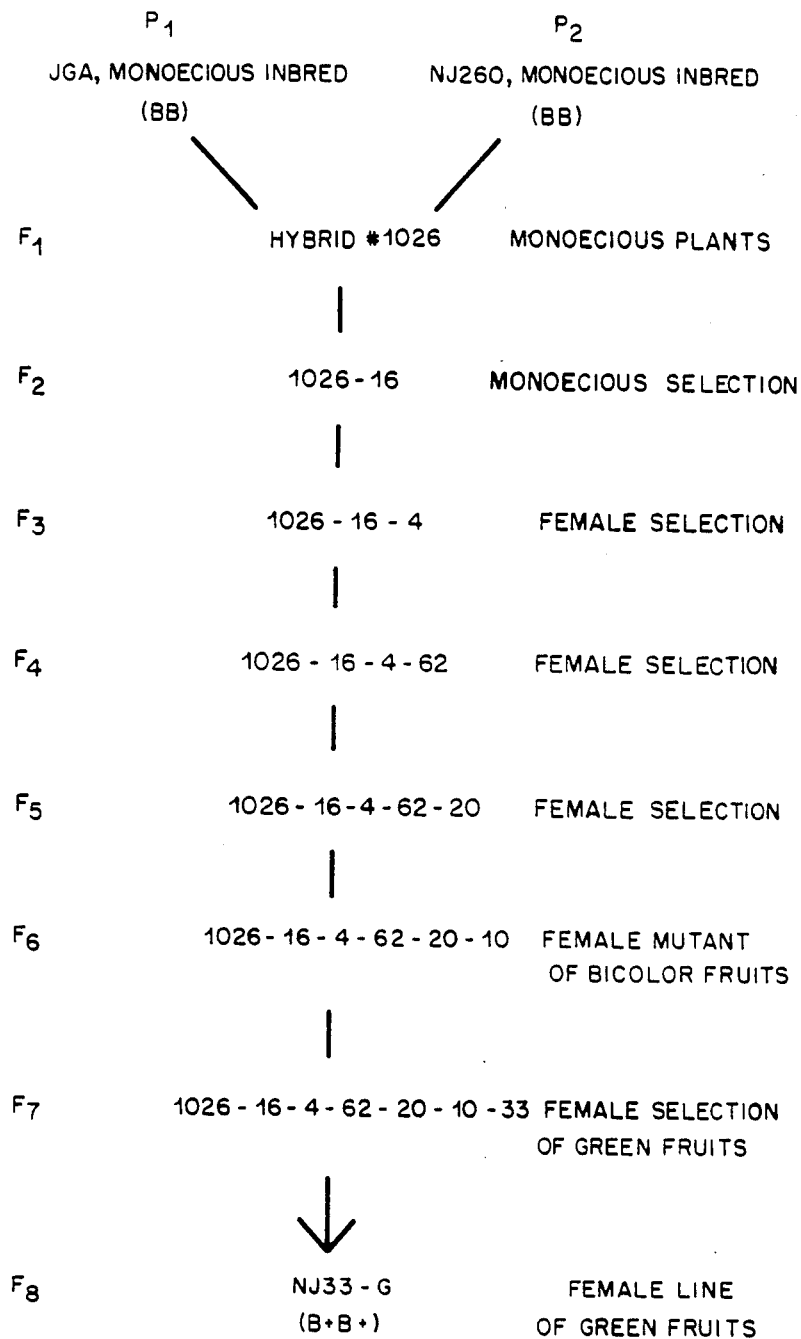

FIG. 4 illustrates the origin of NJ33-G through crossing, self-pollination, and selection. Note the common ancestry of NJ33-G and NJ1 (FIG. 3). NJ33-G is a true-breeding genetic female line whose fruits are green at early bud stages (B+B+), unlike the fruits of its parents which are precociously yellow (BB) at the early bud stages. The green fruits of NJ33-G resulted from a spontaneous mutation of B to B+, a mutation which was responsible for fruit color variation of plant 1026-16-4-62-20-10 (F6). The pedigree shows the relationship of individual plant selections from one generation to the next. Female plants are self-pollinated and reproduced by seed following chemical induction of male flowers. Female individuals were selected for several generations until a true-breeding female line was established. For illustration of mutant 1026-16-4-62-20-10 see FIG. 6, and for illustration of a female plant of NJ33-G see FIG. 7.

Figure 5:
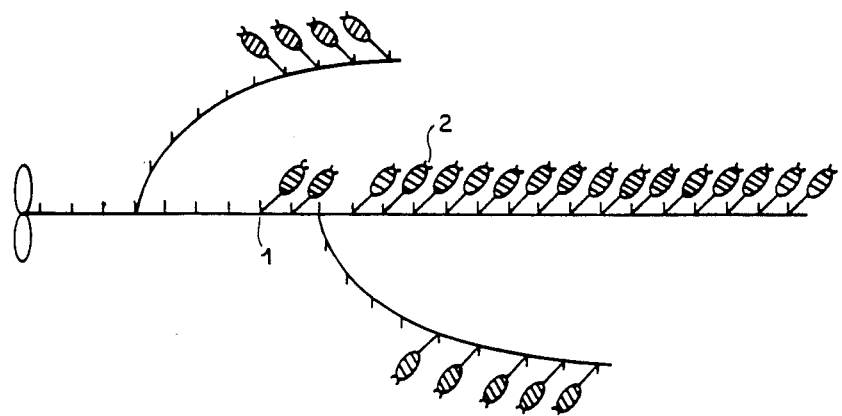

FIG. 5 illustrates a female plant of NJ1. Female plants of NJ1 are 10 to 14 days later in onset of flowering than the parents of NJ1, $P_1$ and $P_2$ (FIG. 3).

The first reproductive leaf axil is designated 1 and the designation 2 is female flower having yellow fruit at early bud stages.

Figure 6:
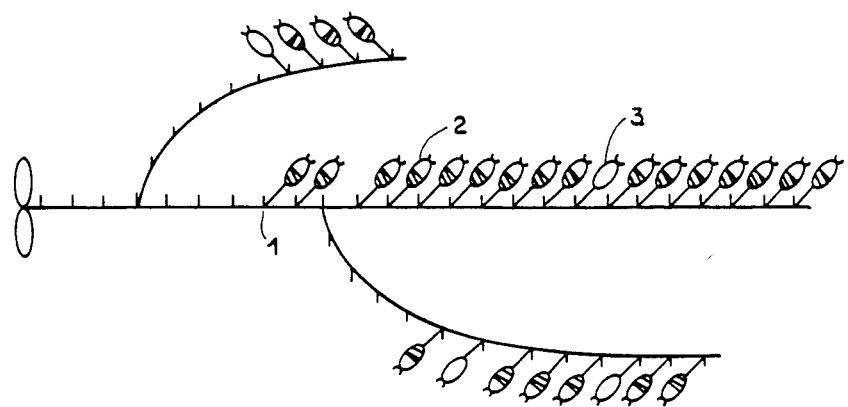

FIG. 6 illustrates the mutant female plant (1026-16-4-62-20-10) which occurred spontaneously in an $F_6$ progeny of the cross JGA×NJ260 (FIG. 4). This mutant produced bicolor as well as green fruits, instead of the expected precociously yellow fruits (BB), and its offspring ($F_7$) consisted of a few green-fruited females (B+B+), one of which was 1026-16-4-62-20-10-33 (FIG. 4).

The first reproductive leaf axil is designated 1. the designation 2 is female flower having bicolor fruit at early bud stages, and the designation 3 is female flower having green fruit at early bud stages.

Figure 7:
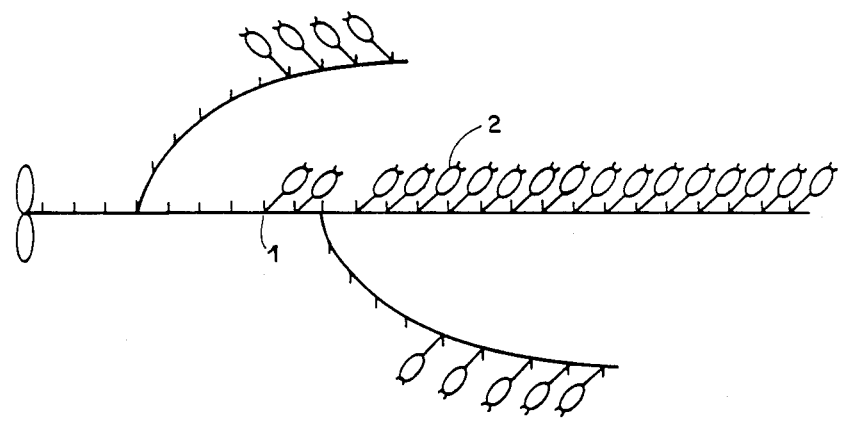

FIG. 7 illustrates a female plant of NJ33-G. The females of NJ33-G are similar to females of NJ1 (FIG. 5) with respect to onset of flowering and several other characteristics, but their fruits are green (B+B+).

The first reproductive leaf axil is designated 1, and the designation 2 is female flower having bicolor fruit at early bud stage, and the designation 3 is female flower having green fruit at early bud stages.

DETAILED DESCRIPTION OF THE INVENTION

The preferred embodiment of this invention for synthesizing genetic females utilizes monoecious inbreds of *Cucurbita pepo* L.

I. Synthesis of Genetic Females and Development of True-Breeding Female Lines in *C. pepo*.

(1) Origin of NJ260: an inbred used in synthesis of genetic females.

Figure 1:
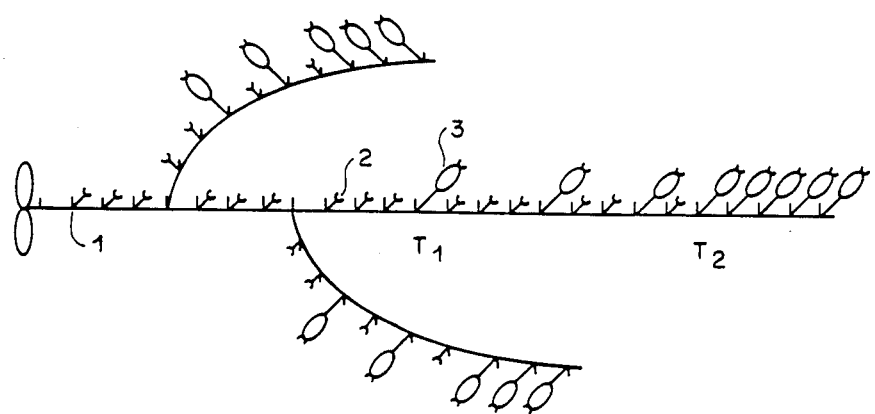
FIG. 1 illustrates the pattern of sex expression during growth and development of a monoecious plant of squash. The plant is made of a main stem, which grows first, and branches. The cotyledonary leaves (seed leaves) are shown at the extreme left of the main stem. The true leaves are not illustrated but their sequential positions are marked. Flowers develop in leaf axils and sex expression turns gradually from maleness to femaleness during plant growth. Thus, a flowering plant consists of 3 sequential phases of reproductive leaf axils: male, transitional (bearing both male and female flowers), and female.

This inbred was developed from a cross of 'Caserta' as seed parent, $P_1$, with 'Precocious Early Prolific' (PEP), $P_2$ (FIG. 2). The 2 parents are early in onset of flowering, monoecious, and strongly female (see FIG. 1 and description of FIG. 1). But they differ in a number of plant and fruit characteristics. A striking difference is in time of fruit pigmentation. At early bud stages, the fruits of Caserta are green due to genes B+B+, while the fruits of PEP are yellow due to genes BB. Caserta is a commercial variety and PEP is a breeding line similar to 'Early Prolific Straightneck', B+B+, except for gene B (For the breeding history of PEP see Shifriss, O. 1981. "Origin, Expression, and Significance of Gene B in *Cucurbita pepo* L. " J. Amer. Soc. Hort. Sci. 106:220-232.) Seed of PEP was deposited in the National Seed Storage Laboratory, C.S.U. Campus, Fort Collins, Colo. 80523, U.S.A., under NSSL Ser. No. 199,054.

The $F_1$ hybrid plants (n=10) of the above cross were monoecious. The second-generation, $F_2$, was obtained through self-pollination of the $F_1$ plants. A small sample of the $F_2$ (n=127) consisted of monoecious plants exclusively. However, some of the $F_2$ segregates were more strongly female than either $P_1$, or $P_2$, or the $F_1$. The most strongly female segregate was a BB plant of pedigree 101-58. Starting with this segregate, a program of self-pollination (inbreeding) and selection for increasing the number of female flowers in plants of subsequent generations led to the development of NJ260 (FIG. 2 and description of FIG. 2). This inbred is unique in several respects, including sex expression (see Shifriss, O. 1981. "Do Cucurbita Plants with Silvery Leaves Escape Virus Infection? Origin and Characteristics of NJ260". Cucurbit Genetics Coop. Rpt. 4:42-43). It begins to flower as a male but soon becomes intensely female, bearing an astonishingly large number of female flower buds. This unusual female intensity is associated with an extra-dwarf habit of growth. No other squash variety or breeding line of such intense female expression was reported in the literature.

(2) Synthesis of genetic females.

The initial step in this synthesis was a cross of 'Jersey Golden Acorn' (JGA) as seed parent, $P_1$, with NJ260, $P_2$ (see FIG. 3 and description of FIG. 3). Both parents are monoecious and both carry genes BB, but they belong to distinctly different groups of varieties. Among other things, JGA is slightly later than NJ260 in onset of flowering and it manifests a relatively strong male expression.

The $F_1$ plants (n=15) of the above cross were monoecious and intermediate between $P_1$ and $P_2$ in female expression. The $F_2$ generation (n=489) consisted of monoecious plants which varied considerably in female expression. One of the $F_3$ progenies obtained from a strongly female $F_2$ segregate, 1026-16, consisted of 2 females and 23 monoecious plants. Female 1026-16-4 was converted to monoecism by spraying it with an aqueous solution of 250 ppm gibberellin 3 (potassium gibberellate, Merck). This female was self-pollinated and small samples of its offspring (n=20 to 25 plants) were tested 6 times under winter (greenhouse) and summer (greenhouse and field) conditions. In winter, the offspring of 1026-16-4 consisted of females and male-sterile plants (producing aborted male flower buds) but in summer it consisted of females and normal monoecious plants of varying degrees of female expression. Moreover, this offspring was later in onset of flowering than the original parents and their $F_1$ hybrid.

Pure female lines were then developed through selection and inbreeding of females in subsequent filial generations. Selection of individual females in each generation was confined to progenies which consisted of increasingly higher female frequency. And selected females were self-pollinated following gibberellin treatment. This selection pressure led to the development of true-breeding female lines between the 6th and the 8th generations ($F_6$–$F_8$). They include NJ1, NJ20, NJ33-G, and NJ34. NJ1 and NJ33-G, are of special practical interest because they are products of more advanced inbred generations and because they represent the 2 systems of fruit pigmentation in *C. pepo*: the standard system (B+B+ varieties) and the precocious system (BB and BB+ varieties).

The breeding history of NJ1 is illustrated in FIG. 3 (see also FIG. 5 as well as the descriptions of FIG. 3 and FIG. 5). Note that NJ1 bears precociously pigmented yellow fruits due to genes BB. This is not surprising because both parents of NJ1, $P_1$ and $P_2$, were BB.

The breeding history of NJ33-G is illustrated in FIG. 4. Note that although NJ33-G and NJ1 (FIG. 3) evolved from the same cross, and the fruits of both parents were yellow due to genes BB, the fruits of NJ33-G are green due to genes B+B+. The origin of these green fruits can be traced to a single mutant plant which occurred spontaneously in a small $F_6$ progeny (n=14) obtained from female 1026-16-4-62-20. The mutant, 1026-16-4-62-20-10, was a female which produced bicolor as well as green fruits (FIG. 6) instead of the expected yellow fruits. The progeny (n=116 females) of this mutant was variable in fruit color, but some of its females produced green fruits exclusively. And the offspring of one of these green-fruited females, 1026-16-4-62-20-10-33, B+B+, gave rise to NJ33-G.

(3) The characteristics of two female lines.

The plants of the NJ1 and NJ33-G are large, of bush growth habit, moderately branched, leaves are mottled or lightly silvery and fruits are Acorn-shaped but taper sharply toward the blossom end. These lines are endowed with an exceptional combining ability as manifested by the extraordinary vigor and high yield of the hybrids obtained from crosses between them and unrelated varieties. With respect to sexual reproduction, the 2 lines are distinguished by 2 features.

First, they are later than their patents in onset of flowering under both short-day and long-day conditions. When sown in the first week of May, under field conditions in New Jersey, they are 10–14 days later in time of flowering than Caserta, JGA, NJ260, PEP, and other varieties noted for early flowering.

Second, they are female throughout plant development under winter greenhouse conditions as well as under controlled conditions of long-days (16 hr), 2400 lux, 20° C. during the light period and 16° C. in the dark. Under summer conditions in New Jersey, these lines are predominantly female, i.e., in addition to a large number of female flowers they produce a few male flowers for short periods of time. For example, when seed is sown in the first week of May, under field conditions in New Jersey, the plants of these lines produce from 50 to 80 female flowers each (if fruit set is prevented) before the appearance of the first few male flowers (based on 1985 data).

Experience in growing NJ1 in Puerto Rico and New Jersey suggests that a combination of relatively high temperatures and high light intensities is conducive for some male expression in this female line.

Technically, NJ1 and NJ33-G are true-breeding phenotypically sensitive female lines. This means that the 2 lines are genetically pure for a potential expression of complete femaleness, but they can produce a few male flowers under certain conditions. The incidence of these male flowers under normal field conditions is within 1–5%.

(4) Genetic basis for variation in female expression.

It is evident that the plants of NJ1 and NJ33-G are distinguished by their late flowering and femaleness. It is also evident that in respect to time of flowering and sex expression the plants of NJ1 and NJ33-G fall outside the limits of variation set by their parents (JGA and NJ260) and the $F_1$ hybrid. Geneticists attribute the appearance of such extreme individuals (genotypes) in a segregating generation to the phenomenon of transgression (see *Glossary of Genetics and Cytogenetics, Classical and Molecular*. 4th rev. ed., by R. Rieger, M. Michaelis, and M. M. Green, Springer-Verlag, Berlin Heidelberg New York, 1976). Therefore, the femaleness in this species originated through transgression (involving recombination of genes) which affected 2 genetic systems. These systems control 2 sequential aspects of reproduction: time of flowering and rate of female flower production.

Reciprocal crosses were made between NJ1 (late flowering, female) and each of Caserta, JGA, and NJ260 (all being relatively early in flowering and monoecious). The results of the reciprocal crosses of each pair of parents were identical. The $F_1$ hybrids of the 3 crosses were relatively early in flowering and monoecious. The $F_2$ generations were difficult to classify, but their distinct features are described and interpreted in the following.

First, each of the $F_2$ generations appeared as a continuum of imperceptible variations in time of flowering, in degree of female expression, and in mode of distribution of female flowers during plant development. The number of female plants in the $F_2$ generations of NJ1×Caserta (n=420), NJ1×JGA (n=111), and NJ1×NJ260 (n=451) was 1, 0, and 4 respectively. In their sex expression these 5 $F_2$ segregates approached the plants of NJ1. Like the plants of NJ1, they were late in flowering and completely female during the early stages of flowering. But unlike the plants of NJ1, they produced male flowers sooner and in a larger number. Thus, in such $F_2$ generations, the estimated proportions of females, identical to those of NJ1, are very low, probably fractions of 140.

The above suggests that the femaleness of NJ1 is brought about through recombination of many genetic elements (polygenes); that these elements reside in different chromosome sites in different varieties; that each of these elements has a small effect; but that cumulatively they can increase dramatically the degree of female expression. This interpretation is compatible with that offered for the origin of NJ1 and NJ33-G through transgression.

Second, some $F_2$ segregates of the cross NJ1×JGA were very late in time of flowering and strongly male. This fact shows that late flowering and femaleness are not causally related.

Third, some $F_2$ segregates of NJ1×Caserta and NJ1×NJ260 were early in flowering and female at early stages of flowering, but at later stages they were essentially monoecious. Other $F_2$ segregates flowered relatively late in their development, branched profusely, produced numerous female flowers more or less simultaneously, but they also produced numerous male flowers. Results of self-pollination for 2 additional generations (i.e., up to $F_4$) showed that the characteristics of these 2 groups of $F_2$ segregates were heritable, and that selection for more intense female expression as well as selection for simultaneous production of female flowers are effective. These results indicate that the present late flowering female lines (at least NJ1) can serve as germplasm for the development of (a) early flowering female lines, and (b) new monoecious varieties adapted to mechanized harvesting.

(5) Essentials for synthesis

The idea that the synthesized females in this species resulted from recombination of many genes and that these genes are distributed unequally in different varieties focuses attention on 2 issues.

First, the chosen parents for crossing should be distantly related and some of these should also exhibit strong female expression. The chosen parents for the first cross which led to the development of NJ260 were Caserta and Precocious Early Prolific (FIG. 2). These varieties are distantly related, but both are strongly female. The chosen varieties for the second cross were JGA and NJ260 (FIG. 3). These varieties are not only distantly related but also different in female expression.

The term "distantly related" refers here to lines known to be of different breeding history as well as of different genetic makeup. But obviously there exist degrees in relatedness. For example, Caserta and Precocious Early Prolific (FIG. 2) belong to the same group of varieties known as Summer Squash, but they are not closely related in breeding history and genetic make-up.

On the other and, JGA and NJ260 (FIG. 3) are more distantly-related from one another than are Caserta from Precocious Early Prolific, JGA being in the group of Winter Squash and NJ260 in the group of Summer Squash varieties.

Some hybrids of crosses between different squash species are predominantly-female (see Pearson, O. H., R. Hopp, and G. W. Bohn. 1951. Notes on spectes crosses in Cucurbita. Proc. Amer. Soc. Hort. Sci. 57:310-322), but thus far no one was able to extract true-breeding female lines from such crosses, partly because the hybrids are highly sterile. Nevertheless, the evidence supports the central idea, emphasized here, that crossing between some distantly related lines often brings together genes for enhanced female expression. Clearly, different species of squash are also distantly related lines. Furthermore, in spite of the high sterility of some interspecific squash hybrids, their sterility can be overcome by "backcrossing" or by other procedures. And the outcome can lead to the development of true-breeding female lines.

Crossing some distantly related lines is essential not only for synthesis of female lines, but also for incorporation in these lines genes for resistance to environmental conditions which favor male expression.

Second, the size of the $F_2$ generation of each cross should be as large as possible, considering cost and effective management. A reasonable estimate is 5000 plants. At a high density (15-30 cm between plants in the row, rows 50-100 cm apart) most of these plants could be eliminated a few days after flowering. Note that the number of $F_2$ plants grown from the cross of Caserta x PEP (FIG. 2) was 127. Several thousand plants of this $F_2$ could have consisted of a few female segregates and/or a few segregates as intensely female as plants of NJ260. Such results would have saved considerable time and effort, and might have dispensed the need for an additional cross such as JGA×NJ260 (FIG. 3).

Thus, an effective procedure for developing true-breeding female lines in monoecious species of plants includes 2 essential requirements: (a) crossing distantly related lines, some of which are strongly female, and (b) selection in large $F_2$ populations and/or in other segregating generations.

II. Hybrid Seed Production in *C. pepo*

(1) Introduction

A program of hybrid seed production consists of three separate operations: reproduction of the seed parent, reproduction of the pollen parent, and production of the hybrid seed. Squash seed growers have the expertise for carrying out these operations successfully. The expertise includes knowledge of favorable production regions; selection of an isolated field for each operation to prevent contamination by foreign pollen; sound cultural practices; use of an effective planting pattern for the 2 parents in the field of hybrid seed production; sowing some parents at different times in order to synchronize their crossing; and the use of bees. The same expertise can be applied to hybrid seed production based on the use of true-breeding female lines as seed parents. However, the use of true-breeding female lines requires special considerations.

(2) Reproduction of a female line

The reproduction of a true-breeding female line such as NJ1 requires the induction of male flowers by a chemical agent that does not adversely affect plant growth. This chemical induction can be brought about by gibberellin 3 ($GA_3$), a different gibberellin, a combination of gibberellins, silver nitrate, or other male-inducing chemical agents. Present knowledge is based largely on the use of $GA_3$ under greenhouse conditions. Therefore, critical testing is essential before the best treatment is adopted with respect to choice of the chemical agent, concentration, time of application, the number of applications, and the response of a particular female line to the chemical agent in a given environment. In addition, the successful reproduction of a true-breeding female line depends on adequate isolation distance from other plants of *C. pepo* as well as on the presence of a sufficient number of bees whose activity is not diverted to more enticing plant species in the vicinity.

(3) Favorable environment

A region of moderate temperatures during spring and early summer is best suited for hybrid production based on the use of a true-breeding female line. At moderate temperatures, favorable to squash growth, the seed parent is expected to be either strictly female or essentially female. If it produces a few male flowers, these will result in little, if any, self-pollinated seed, becuase of the overwhelming number of female flowers in the seed parent and the large number of male flowers in the pollen plant. Therefore, the resulting seed of the true-breeding female line is expected to be essentially hybrid, i.e., over 95%.

In an environment of excessively high temperatures and/or under other adverse environmental conditions, the incidence of male flowers in a true-breeding female line may rise above a tolerable level. If so, it may be necessary to apply 1 or 2 treatments with Ethephon or with another chemical that suppresses the development of normal male flowers.

Thus, it is advisable to gain experience in reproducing true-breeding female lines as well as in using them in hybrid production before attempting commercial production.

(4) Need of new female lines

Although NJ1 and NJ33-G can be used for production of some excellent hybrids, there is a need for hybrids of a wide range of horticultural characteristics. This can be accomplished by transferring the genetic material for femaleness from NJ1 or NJ33-G into the backgrounds of inbreds which represent the major groups of varieties in *C. pepo*.

III. Development of True-Breeding Female Lines in Monoecious Species other than *C. pepo*.

The procedure for synthesis of genetic females and development of true-breeding female lines used in *C. pepo* can be adopted in each of the 4 other cultivated species of Cucurbia (*C. ficifolia, C. maxima, C. mixta,* and *C. moschata*).

Alternatively, the genetic material for femaleness in *C. pepo* could be transferred to each of the 4 cultivated species of Cucurbita. However, attempts to transfer genes from one species of Cucurbita to another often meet serious if not insurmountable difficulties. The transfer of genes from *C. pepo* to *C. moschata* is relatively easy, but the transfer of genes from *C. pepo* to *C. maxima* or to other species may require the use of special bridges (see review in Cucurbits by T. W. Whitaker and G. N. Davis, Interscience Publications, Inc., New York, 1962; see also Rhodes, A. M. 1959. Species Hybridization and Interspecific Gene Transfer in the Genus Cucurbita. Proc. Amer. Soc. Hort. Sci. 74: 546–551; and Whitaker, T. W. 1956. The Origin of the Cultivated Cucurbita. Amer. Naturalist 90:171–176). The term "bridge" refers here to a particular variety or a particular population (gene pool) within a group of species. This variety or population is more compatible genetically to most or all of the species involved than any other variety or population within this group.

The procedure for synthesis of genetic females and development of true-breeding female lines used in *C. pepo* can be adopted in any monoecious species of plant genera other than Cucurbita provided the species involved exhibits considerable genetic diversity and the genetic control of female expression is similar to that in *C. pepo*.

What is claimed is:

1. A process for synthesizing true-breeding female lines of squash comprising:
   (a) selecting one monocious variety or inbred as seed parent ($P_1$) and another monoecious variety or inbred as the pollen parent ($P_2$), at least one of which is strongly female, said parents being different in breeding history and in genetic makeup;
   (b) crossing $P_1$ and $P_2$;
   (c) growing $F_1$ generation from the seed resulting from step (b);
   (d) self pollination of the $F_1$ generation;
   (e) growing $F_2$ generation plants from the seeds resulting from step (d);
   (f) selecting an $F_2$ segregate which has very strong female expression or is female; and
   (g) developing a true-breeding female line from said segregate through selection and self-pollination in subsequent filial generation.

2. A process of claim 1 wherein the squash parents are selected from a single species, *Cucurbita pepo* L.

3. A process of claim 2 wherein one of squash parents is a breeding line known as NJ260.

4. A process of claim 2 wherein one parent is a variety known as Jersey Golden Acorn, and the other parent is a breeding line known as NJ260.

5. A process of claim 4 wherein the synthesized true-breeding female line is NJ1.

6. A process of claim 4 wherein the synthesized true-breeding female line is NJ33-G.

7. A process of claim 2 wherein the fruits of the synthesized true-breeding female line are green at early bud stage.

8. A process of claim 2 wherein the fruits of the synthesized true-breeding female line are yellow at early bud stage.

9. A process of claim 1 wherein the squash parents are selected from a single species, *Cucurbita ficifolia* Bouché.

10. A process of claim 1 wherein the squash parents are selected from a single species, *Cucurbita maxima* Duch.

11. A process of claim 1 wherein the squash parents are selected from a single species, *Cucurbita mixta* Pang.

12. A process of claim 1 wherein the squash parents are selected from a single species, *Cucurbita moschata* Poir.

13. A process of claim 1 wherein both squash parents are strongly female.

14. A process of claim 1 wherein the squash parents belong to different species of Cucurbita.

15. A process of claim 1 in which hybrid sterility in $F_1$ generation is overcome by backcrossing to either one of the parents or to another variety or inbred.

16. A process for synthesizing true-breeding female lines of the Curcurbitaceae family comprising:
   (a) selecting one monoecious variety or inbred as seed parent ($P_1$) and another monoecious variety or inbred as pollen parent ($P_2$), at least one of which is strongly female, said parents being different in breeding history and in genetic makeup:
   (b) crossing $P_1$ and $P_2$;
   (c) growing $F_1$ generation from the seed resulting from step (b);
   (d) self-pollinating of $F_1$ generation;
   (e) growing $F_2$ generation plants from the seeds resulting from step (d);
   (f) selecting an $F_2$ segregate which has very strong female expression or is female; and
   (g) developing a true-breeding female line from said segregate through selection and self-pollination in subsequent filial generations.

17. A process for synthesizing true-breeding female lines in monoecious species of crop plants comprising:
   (a) selecting one monoecious variety or inbred as seed parent ($P_1$) and another monoecious variety or inbred as pollen parent ($P_2$), at least one of which is strongly female, said parents being different in breeding history and in genetic makeup.
   (b) crossing $P_1$ and $P_2$;
   (c) growing $F_1$ generation from the seed resulting from step (b);
   (d) self-pollinating of $F_1$ generation;
   (e) growing $F_2$ generation plants from the seeds resulting from step (b);
   (f) selecting an $F_2$ segregate which has very strong female expression or is female; and
   (g) developing a true-breeding female line from said segregate through selection and self-pollination in subsequent filial generations.

18. A method of producing hybrid squash seed using a true-breeding female line as seed parent in pollinating proximity to another line of squash which serves as pollen parent and harvesting the seed.

19. A method of claim 18 wherein the species of the true-breeding female line is *Cucurbita pepo* L.

20. A method of claim 18 wherein the true-breeding female line is a descendant of a cross in which one of the parents was a breeding line known as NJ260.

21. A method of claim 18 wherein the true-breeding female line is a descendant of a cross in which one parent was a variety known as Jersey Golden Acorn and the other parent was a breeding line known as NJ260.

22. A method of claim 18 wherein the true-breeding female line is NJ1.

23. A method of claim 18 wherein the true-breeding female line is NJ33-G.

24. Hybrid squash seed produced by using a true-breeding female line as seed parent in pollinating proximity to another line of squash which served as pollen parent.

25. Hybrid squash seed of claim 24 wherein the true-breeding female line is *Cucurbita pepo* L.

26. Hybrid squash seed of claim 24 wherein the true-breeding line is a descendant of a cross in which one of the parents was a breeding line known as NJ260.

27. Hybrid squash seed of claim 24 wherein the true-breeding female line is a descendant of a cross in which one of the parents was the variety known as Jersey Golden Acorn and the other parent was a breeding line known as NJ260.

28. Hybrid squash seed of claim 24 wherein the true-breeding female line is NJ1.

29. Hybrid squash seed of claim 24 wherein the true-breeding line is NJ33-G.

30. A first generation squash plant, the plant having been grown from the seed resulting from crossing a true-breeding female line as seed parent in pollinating proximity to another line of squash which serves as pollen parent.

31. A first generation squash plant of claim 30 wherein the parents are selected from a single species, *Cucurbita pepo* L.

32. A first generation squash plant of claim 30 wherein the true-breeding female line is a descendant of a cross in which one of the parents was a breeding line known as NJ260.

33. A first generation squash plant of claim 30 wherein the true-breeding female line is a descendant of a cross in which one of the parents was the variety known as Jersey Golden Acorn and the other parent was a breeding line known as NJ260.

34. A first generation squash plant of claim 30 in which the true-breeding female line is NJ1.

35. A first generation squash plant of claim 30 in which the true-breeding female line is NJ33-G.

36. Squash seed which when grown yields a true-breeding female line.

37. Squash seed of claim 36 which when grown yields a true-breeding female line of the species *Cucurbita peco* L.

38. Squash seed of claim 36 which when grown yields a true-breeding female line which is a descendant of a cross in which NJ260 was a parent.

39. Squash seed of claim 36 which when grown yields a true-breeding female line which is a descendant of a cross in which one of the parents was the variety known as Jersey Golden Acorn and the other parent was a breeding line known as NJ260.

40. Squash seed of claim 36 which when grown yields the true-breeding female line NJ1.

41. Squash seed of claim 36 which when grown yields the true-breeding female line NJ33-G.

42. A true-breeding female line of squash selected from the following species of the botannical genus Cucurbita: *C. ficifolia* Bouché, *C. maxima* Duch., *C. mixta* Pang., *C. moschata* Poir, and *C. peno* L.

43. A true-breeding female line of squash of claim 42 wherein said line is *Cucurbita ceoo* L.

44. A true-breeding female line of squash of claim 42 wherein said line is a descendant of a cross in which NJ260 was a parent.

45. A true-breeding female line of squash of claim 42 wherein said line is a descendant of a cross in which one of the parents was the variety known as Jersey Golden Acorn and the other parent was a breeding line known as NJ260.

46. A true-breeding female line of squash of claim 42 which is NJ1.

47. A true-breeding female line of squash of claim 42 which is NJ33-G.

48. A process for synthesizing a true-breeding female line of squash comprising:
 (a) selecting an existing true-breeding female line as seed parent ($P_1$) and another line as pollen parent ($P_2$);
 (b) crossing $P_1$ and $P_2$;
 (c) growing $F_1$ generation from the seed resulting from step (b);
 (d) self-pollination of the $F_1$ generation;
 (e) growing $F_2$ generation plants from the seeds resulting from step (d);
 (f) selecting an $F_2$ segregate which has intense female expression or is female and which has one or more improved horticultural characteristics; and
 (g) developing a true-breeding female line having the one or more improved horticultural characteristics, from said segregate through selection and self-pollination in subsequent filial generations.

49. A process of claim 48 wherein the squash parents are selected from a single species, *Cucurbita pepo* L.

50. A process of claim 48 wherein the existing true-breeding female line is a descendant of a cross in which one of the parents was NJ260.

51. A process of claim 48 wherein the existing true-breeding female line is a descendant of a cross in which one of the parents was the variety known as Jersey Golden Acorn and the other parent was a breeding line known as NJ260.

52. A process of claim 48 wherein the existing true-breeding female line is NJ1.

53. A process of claim 48 wherein the existing true-breeding female line is NJ33-G.

54. A process for synthesizing new monoecious varieties of squash comprising:
 (a) selecting an existing true-breeding female line as seed parent ($P_1$) and a monoecious variety as pollen parent ($P_2$);
 (b) crossing $P_1$ and $P_2$;
 (c) growing $F_1$ generation from the seed resulting from step (b);
 (d) self-pollination of the $F_1$ generation;
 (e) growing $F_2$ generation plants from the seeds resulting from step (d);
 (f) selecting an $F_2$ monoecious segregate having one or more improved horticultural characteristics; and
 (g) developing a monoecious variety having the one or more improved horticultural characteristics from said segregate through selection and self-pollination in subsequent filial generations.

55. A process of claim 54 wherein the squash parents are selected from a single species, *Cucurbita pepo* L.

56. A process of claim 54 wherein the existing true-breeding female line is a descendant of a cross in which one of the parents was NJ260.

57. A process of claim 54 wherein the existing true-breeding female line is a descendant of a cross in which one of the parents was the variety known as Jersey Golden Acorn and the other parent was a breeding line known as NJ260.

58. A process of claim 54 wherein the existing true-breeding female line is NJ1.

59. A process of claim 54 wherein the existing true-breeding female line is NJ33-G.

* * * * *